United States Patent [19]
Carter

[11] Patent Number: 5,779,678
[45] Date of Patent: *Jul. 14, 1998

[54] FLUID ADMINISTRATION APPARATUS

[75] Inventor: Roland Henry Clyne Carter, Hythe, England

[73] Assignee: Smiths Industries plc, London, England

[*] Notice: This patent issued on a continued prosecution application filed under 37 CFR 1.53(d), and is subject to the twenty year patent term provisions of 35 U.S.C. 154(a)(2).

[21] Appl. No.: 754,971

[22] Filed: Nov. 22, 1996

[30] Foreign Application Priority Data

Dec. 2, 1995 [GB] United Kingdom ............. 9524880

[51] Int. Cl.⁶ .................................................. A61M 37/00
[52] U.S. Cl. ............................. 604/140; 128/DIG. 12; 604/143
[58] Field of Search ........................... 604/131, 140, 604/141, 142, 143, 146, 151; 128/DIG. 12

[56] References Cited

U.S. PATENT DOCUMENTS

| | | | |
|---|---|---|---|
| 3,889,677 | 6/1975 | Nehring | 604/142 |
| 4,085,749 | 4/1978 | Chambron | 604/143 |
| 4,351,335 | 9/1982 | Whitney et al. | 604/143 |
| 4,505,701 | 3/1985 | Navato | 604/143 |
| 5,024,656 | 6/1991 | Gasaway et al. | 604/141 X |
| 5,059,182 | 10/1991 | Laing | 604/142 |
| 5,098,418 | 3/1992 | Maitz et al. | 604/141 X |
| 5,312,389 | 5/1994 | Theeuwes et al. | 604/141 X |

FOREIGN PATENT DOCUMENTS

| | | |
|---|---|---|
| 0 523 456 | 1/1993 | European Pat. Off. . |
| 0523456 | 1/1993 | European Pat. Off. . |
| 2848433 | 5/1979 | Germany .......... 604/143 |
| WO 93/00944 | 1/1993 | WIPO . |

*Primary Examiner*—Michael A. Brown
*Attorney, Agent, or Firm*—Pollock, Vande Sande & Priddy

[57] ABSTRACT

PCA apparatus has a container with a movable piston dividing the container into a lower chamber for medication liquid and an upper, air-filled chamber. A manually-actuated air pump is connected to the upper chamber so that air can be supplied to the upper chamber to displace the piston and discharge the liquid through a catheter. The air pump has a cylinder containing a plunger with a capillary inlet, to limit the rate at which air can flow into the cylinder and hence be pumped to the upper chamber. The lower chamber is filled through a removable inlet spike connector by pulling up the piston with an actuating rod projecting from the upper end of the container. The rod is frangible so that it can be removed after filling the lower chamber.

17 Claims, 2 Drawing Sheets

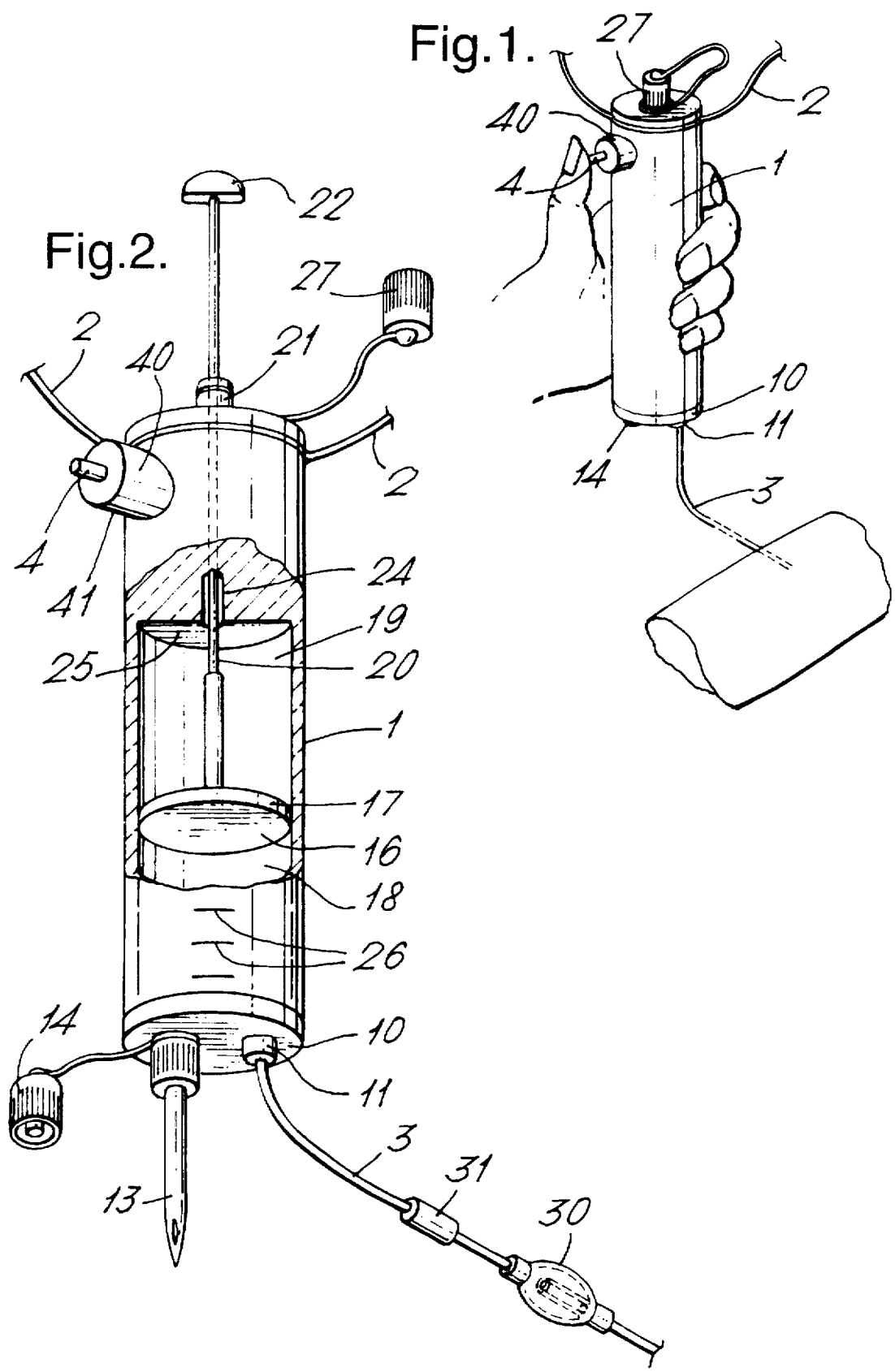

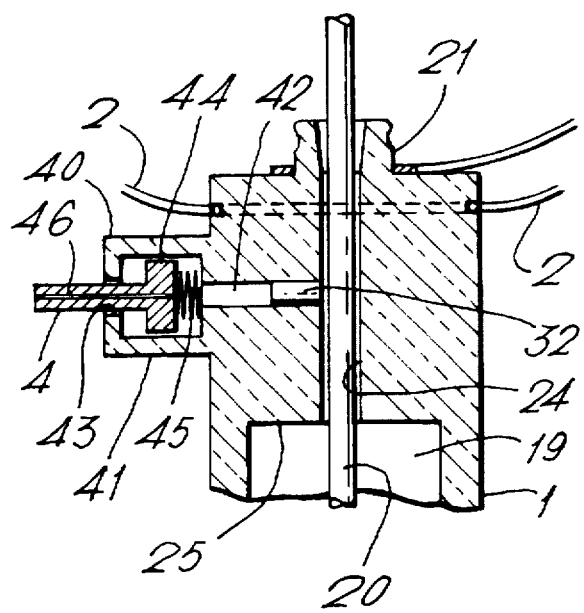
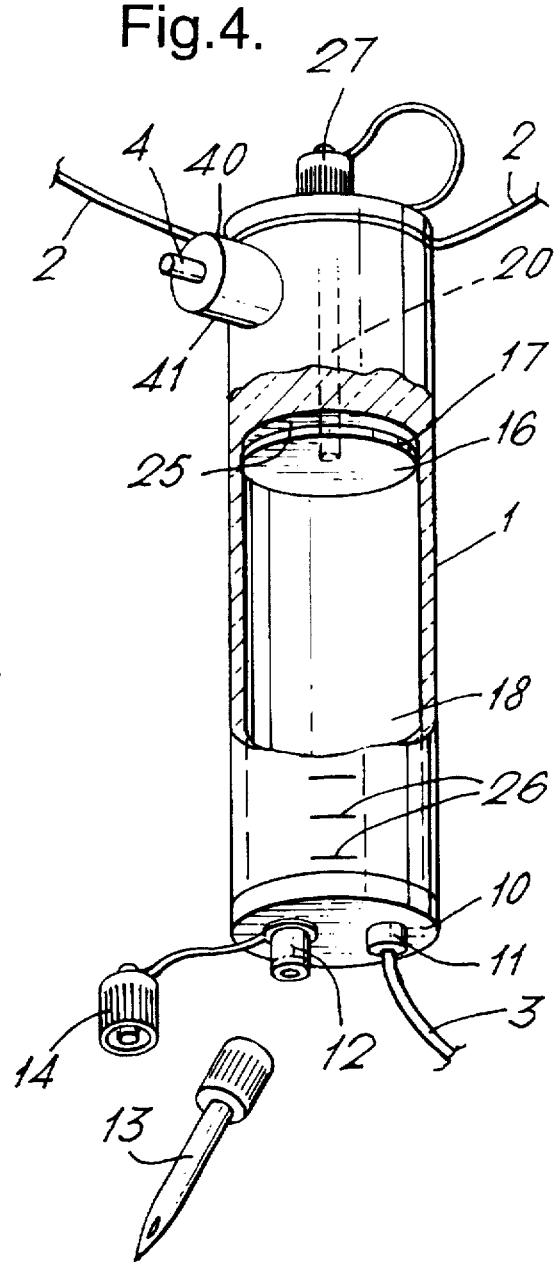

FLUID ADMINISTRATION APPARATUS

BACKGROUND OF THE INVENTION

This invention relates to fluid administration apparatus.

The invention is more particularly concerned with apparatus by which a patient can administer doses of medication to himself when desired, such as patient-controlled analgesia apparatus, or PCA.

Where doses of medication such as analgesia, antibiotic or the like have to be administered frequently, it is often preferable to use some form of pump connected to an implanted catheter, rather than make repeated injections. A review of PCA apparatus is given in "Patient-Controlled Analgesia: A review of Effectiveness of Therapy and a Evaluation of Currently Available Devices" by R. P. Rapp et al., DICP, The Annals of Pharmacotherapy, November 1989, Volume 23, pages 899 to 903. Some presently-available apparatus have an electrically-controlled pump and employ a computer to monitor the dose of medication administered. Examples of this form of apparatus are described in: "Patient controlled analgesia—Assessment of machine feedback to patients" by T. W. Johnson and F. E. Luscombe, Anaesthesia 1992, Volume 47, pages 899 to 901 and U.S. Pat. No. 5,069,668. These apparatus are complex and expensive, and can be difficult to set up.

In many applications, medication only needs to be administered at irregular intervals, such as when the patient feels the need for additional analgesia. A manually-operated pump or similar device is preferable in these circumstances because it can give the optimum administration of the medication. Manually-operated pumps can be of simple, low-cost construction, and can be light in weight and compact compared with electrical pumps. One such pump is described in PCT/GB 9401831. This pump has a resilient chamber with a capillary inlet by which fluid from a reservoir enters the chamber. The outlet from the pump has a one-way valve, which opens when the chamber is squeezed to allow fluid to be expelled to the patient. When the chamber is released, the one-way valve closes and fluid is drawn into the chamber via the capillary, which controls the rate at which the chamber can be filled and hence limits administration to a safe level. Other examples of manually-operated pumps are described in WO-A-91/08002, EP-A-231371, WO-A-93/00944, FR-A-2215246, FR-A-2338710, EP-A-0483759, WO 91/08002 and U.S. Pat. No. 3,035,575. Some apparatus is designed specifically to be implanted under the skin of the patient so that the medication reservoir has to be refilled by injection through the skin. The medication pump is activated by pushing down the skin over the pump. In many cases patients can have difficulty in locating the correct location, especially elderly patients with poor manual dexterity. Examples of implantable apparatus are described in EP-A-168675, EP-A-143503 and U.S. Pat. No. 4,857,059.

These previous forms of apparatus have various disadvantages. Where a capillary is used to control the flow of liquid, this can become blocked easily. If the pump is connected to a separate medication reservoir by a length of tubing, the apparatus is difficult to carry around and the tubing is prone to tangling or occlusion.

BRIEF SUMMARY OF THE INVENTION

It is an object of the present invention to provide improved fluid administration apparatus.

According to one aspect of the present invention there is provided fluid administration apparatus having a container with a first chamber and a second chamber separated from one another by a displaceable wall, the first chamber being adapted for containing a medication liquid and having an outlet adapted to be connected to a region of the patient, the second chamber being air-filled and having an inlet coupled to the outlet of manually-actuable air pump means, and the air pump means having an air inlet with an air flow restrictor to limit flow of air into the air pump means such that when the air pump means is actuated it supplies air to the second chamber and displaces the displaceable wall and drives liquid out of the outlet of the first chamber to the region of the patient.

The air pump preferably includes a plunger slidable along a cylinder, the air pump including a spring arranged to urge the plunger to one end of the cylinder. The air flow restrictor may be located in the plunger such as to allow air flow into the cylinder through the plunger. The air flow restrictor is preferably a capillary.

According to another aspect of the present invention there is provided fluid administration apparatus having a container with a first chamber and a second chamber separated from one another by a displaceable wall, the first chamber being adapted for containing a medication liquid and having an outlet adapted to be connected to a region of the patient, the second chamber being air-filled and having an inlet coupled to the outlet of manually-actuable air pump means, and the air pump means being arranged to supply air to said second chamber and thereby displace said displaceable wall such that liquid is driven out of the outlet of the first chamber, the air pump being operable such that only a limited amount of air can be supplied to the second chamber in a predetermined time despite how often said pump is actuated, so as thereby to limit the amount of medication liquid administered to the patient.

The displaceable wall may be provided by a piston. The container preferably has an inlet opening into the first chamber, the piston having an actuating rod arranged to project from the container such that liquid can be drawn into the first chamber through said inlet by moving said actuating rod. The actuating rod is preferably removable from the piston and may be frangible. The piston may be arranged to extend through a bore at one end of the container, the apparatus including a cap for closing the bore. The apparatus preferably includes a one-way valve between said air pump and said second chamber. The inlet opening into the first chamber may include a removable spike connector. The apparatus may include a necklace attached to the container by which the apparatus can be worn about the neck of the user. At least a part of the container is preferably transparent.

PCA apparatus in accordance with the present invention, will now be described, by way of example, with reference to the accompanying drawings.

BRIEF DESCRIPTION OF THE DRAWINGS

FIG. 1 is a perspective view showing the apparatus in use;

FIG. 2 is an enlarged, perspective, partly cut-away view of the apparatus;

FIG. 3 is a further enlarged sectional side elevation of a part of the apparatus; and FIG. 4 is a perspective, partly cut-away view of the apparatus after loading.

DETAILED DESCRIPTION OF THE PREFERRED EMBODIMENT

The PCA apparatus has a cylindrical container 1 that is worn about the neck by means of a necklace 2. The patient can administer doses of analgesia via a catheter 3 by depressing a plunger 4.

The container 1 is of a transparent plastics material, such as polycarbonate, compatible with the liquid medication contained within it. Typically, the container 1 is about 30 mm in diameter and about 100 mm long, giving it a capacity of about 70 ml. At its lower end, the container 1 is closed by an end cap 10 having an outlet collar 11 into which the machine end of the catheter 3 is sealed. The catheter 3 is a conventional intravenous catheter and has a filter 30 with a hydrophobic vent, which allows air bubbles to escape, preventing them being passed to the patient, and traps any particles in the medication. A one-way valve 31 allows flow of fluid along the catheter 3 out of the container but prevents flow in the opposite direction. The end cap 10 also has a female luer lock inlet 12, which is attached to a spike connector 13 and which can be closed, after removal of the spike, by a luer cap 14.

A piston 16 with a seal 17 around its outer edge makes a sliding seal with the inside of the container 1. The piston 16 forms a wall dividing the container into a first or lower chamber 18 and a second or upper chamber 19 of variable sizes. The lower chamber 18 contains liquid analgesia medication; the upper chamber 19 is filled with air. The piston 16 is connected to an actuating rod 20 of a frangible plastics material, which extends upwardly, axially of the container 1. The upper end of the container 1 is closed and is provided with a central female luer projection 21 through which the actuating rod 20 extends. The actuating rod 20 is reduced in thickness from a point about 30 mm from the piston 16 and has a handle 22 at its upper end.

At its upper end, the internal diameter of the container 1 is reduced to about 5 mm, forming a narrow, axial bore 24, about 30 mm long, communicating with the luer projection 21. The bore 24 is wide enough to receive the actuating rod 20 and to allow air to flow around the outside of the rod. A step 25 is formed between the main part of the inside of the container 1 and the bore 24, which provides a stop to limit upward displacement of the piston 16.

On one side of the upper end of the container 1 there is a manually-actuable air pump 40. The pump 40 comprises a short, radially-projecting cylinder or barrel 41 opening at its inner end into the bore 24 via a radial air passage 42. A one-way valve 32, such as a ball valve or duck-bill valve, is located at the inner end of the air passage 42. The valve 32 allows air to flow out of the pump 40 into the bore 24 and the upper chamber 19 but prevents flow in the opposite direction. The barrel 41 has a reduced diameter opening 43 at its outer end through which projects one end of a plunger 4, the projecting end of the plunger forming a button the user can press in. The other end of the plunger 4 has a sliding seal 44 with the inside of the barrel and is urged outwardly by a helical spring 45. A capillary bore 46 extends axially along the plunger 4 to allow a restricted flow of air into the barrel 41. The capillary 46 need not extend through the plunger 4 itself but could, for example, extend through the wall of the barrel 41.

Initially, the piston 16 is located at the lower end of the container 1. The apparatus is filled with liquid medication by pushing the spike 13 into the loading port of a bag or other reservoir (not shown), gripping the handle 22 and pulling the actuating rod 20 up to its fullest extent so that the piston 16 abuts the stop 25. Air in the upper chamber 19 can escape from the container 1 during filling via the bore 24, around the outside of the rod 20, and the projection 21. The transparent nature of the container 1 enables the position of the piston 16 to be viewed against graduations 26 along the container. When the apparatus has been filled, the spike 13 is removed, as shown in FIG. 4, and the inlet 12 is closed by the cap 14. The reduced thickness part of the actuating rod 20 projects from the luer projection 21 and this is snapped off at the junction with the thicker, lower part of the rod and is discarded. For reduced quantities, the rod 20 may be pulled up to a limited extent and the rod removed by unscrewing from the piston 16. Alternatively, the rod could be snapped off at any length.

The luer projection 21 is then closed with a luer cap 27, which prevents escape of air from the bore 24. The luer cap 27 has a tapered male formation, which projects into the bore 24. When this is inserted, it contacts the remaining length of the rod and pushes it down a short distance. This has the effect of discharging a small amount of liquid into the catheter 3 and thereby primes it. If the rod is unscrewed, the catheter can be primed using the pump 40. The apparatus is hung about the neck of the patient by the necklace 2. The container could be prefilled with medication, in which case there would be no need for a medication fluid inlet 12.

When the patient feels the need for a dose of analgesia, he presses in the plunger 4 against the action of the spring 45. This displaces air out of the barrel 41, along the air passage 42 and into the upper chamber 19 via the bore 24. The pressure in the upper chamber 19 is thereby increased above that in the lower chamber 18 and causes the piston 16 to be displaced down to equalize these pressures. Movement of the piston 16 forces a small amount of liquid (typically about 0.5–1.0 ml) out of the lower chamber 18 and to the patient, via the catheter 3. The plunger 4 remains depressed despite the action of the spring 45, because flow of air into the barrel is restricted by the capillary 46. Typically, it takes about 3 to 5 minutes for the plunger to be displaced outwardly to its fullest extent by the spring 45. Because the air pump 40 can only supply a limited amount of air to the upper chamber in a predetermined time, despite how often the pump is actuated, the rate of administration of medication is effectively limited. Even if the patient were to depress the plunger 4 before it was fully extended, this would only allow a reduced dose of medication to be administered.

The apparatus has advantages over previous fluid-administration apparatus. It is of a relatively simple, low cost construction and can be manufactured reliably. Because the liquid medication does not have to flow through a capillary, there is a reduced risk of blockage. The apparatus is self contained and, once filled, it does not need to be connected to a separate fluid reservoir. The apparatus is also easier to fill and prime than previous apparatus. Furthermore, the patient and doctor can readily see how much medication has been administered.

It will be appreciated that the apparatus could be used to administer other forms of liquid medication and is not confined to analgesia. Instead of a movable piston, other forms of movable wall could be used, such as a flexible diaphragm. Means other than a capillary air flow restrictor could be used to limit the amount of air that can be supplied to the upper chamber in a predetermined time.

What I claim is:

1. Fluid administration apparatus comprising:
    a container;
    a first chamber in said container, said first chamber being adapted for containing a medication liquid and having an outlet adapted to be connected to a region of a patient;
    a second chamber, said second chamber being air-filled and having an inlet;

a movable piston separating said first and second chambers from one another;

a manually-actuable air pump, said pump having an internal volume and an air inlet into said internal volume, said air inlet including an air flow restrictor arranged to limit flow of air from outside the apparatus into said internal volume; and a connection between said internal volume of said air pump and said inlet of said second chamber, such that said air pump can be repeatedly manually actuated to supply air to said second chamber and thereby progressively displace said piston further on each actuation so as to drive liquid out of said outlet of said first chamber.

2. Fluid administration apparatus according to claim 1, wherein said first chamber has an inlet by which liquid can be drawn into said first chamber, wherein said piston has an actuating rod, and wherein said actuating rod is arranged to project from the container such that liquid can be drawn into said first chamber by moving said actuating rod.

3. Fluid administration apparatus according to claim 2, wherein said actuating rod is removable from said piston.

4. Fluid administration apparatus according to claim 3, wherein said actuating rod is frangible.

5. Fluid administration apparatus according to claim 3, wherein said container has a bore at one end, wherein said piston is arranged to extend through said bore at one end of the container, and wherein said apparatus includes a cap for closing said bore.

6. Fluid administration apparatus according to claim 1, wherein said air pump includes a plunger and a cylinder, and wherein said plunger is slidable along said cylinder.

7. Fluid administration apparatus according to claim 6, wherein said air pump includes a spring arranged to urge said plunger to one end of said cylinder.

8. Fluid administration apparatus according to claim 6, wherein said air flow restrictor is located in said plunger such as to allow air flow through said plunger into said cylinder.

9. Fluid administration apparatus according to claim 1 including a one-way valve between said air pump and said second chamber.

10. Fluid administration apparatus according to claim 1, wherein said air flow restrictor is a capillary.

11. Fluid administration apparatus according to claim 1, wherein said container includes an inlet opening into said first chamber.

12. Fluid administration apparatus according to claim 11, wherein said inlet opening into said first chamber includes a removable spike connector.

13. Fluid administration apparatus according to claim 1, including a necklace attached to said container by which said apparatus can be worn about the neck of the user.

14. Fluid administration apparatus according to claim 1, wherein at least a part of said container is transparent.

15. Fluid administration apparatus comprising:

a container;

a first chamber in said container, said first chamber being adapted for containing a medication liquid, said first chamber having an outlet adapted to be connected to a region of a patient, and an inlet through which medication liquid can be drawn into the first chamber;

a second chamber, said second chamber being air-filled and having an inlet;

a piston movable along said container, said piston separating said first and second chambers from one another, said piston having an actuating rod projecting from the container by which said piston can be pulled along the container to draw medication liquid into said first chamber through said inlet of said first chamber, and said actuating rod being removable from said piston after filling;

a manually-actuable air pump, said pump having an air inlet including an air flow restrictor arranged to limit flow of air into said air pump; and a connection between said air pump and said inlet of said second chamber, such that when said air pump is actuated it supplies air to said second chamber and displaces said piston such that liquid is driven out of said outlet of said first chamber.

16. Fluid administration apparatus comprising:

a container;

a first chamber in said container, said first chamber being adapted for containing a medication liquid and having an outlet adapted to be connected to a region of a patient;

a second chamber, said second chamber being air-filled and having an inlet;

a displaceable wall separating said first and second chambers from one another; and an air pump, said pump having a cylinder, a one-way valve at an outlet of said cylinder, a manually actuable plunger located in said cylinder, said plunger being manually displaceable along the cylinder in one direction to displace air out of said cylinder via said one-way valve and into said inlet of said second chamber such as thereby to displace said displaceable wall and displace medication liquid out of said outlet of said first chamber, a spring arranged to displace said plunger along said cylinder in the opposite direction, and a restricted flow air inlet from outside the apparatus into said cylinder so that when said plunger is released, said spring displaces said plunger in said opposite direction and draws air from outside the apparatus into said cylinder through said restricted flow air inlet, said plunger being repeatedly actuable to progressively displace said wall further and to displace additional volumes of medication liquid out of said outlet on each actuation.

17. PCA apparatus comprising:

a container;

a first chamber in said container, said first chamber being adapted for containing an analgesic liquid, said first chamber having an outlet connected to a catheter, and a closable inlet by which said analgesic liquid can be introduced to said first chamber;

a second chamber, said second chamber being air-filled and having an inlet;

a displaceable wall separating said first and second chambers from one another;

an air pump having an internal volume and a manually-displaceable button operable to displace air out of said pump, and an air inlet connecting said internal volume to outside said apparatus, said air inlet including an air flow restrictor arranged to limit flow of air into said internal volume of said air pump from outside the apparatus; and a connection between an outlet of said internal volume of said air pump and said inlet of said second chamber, such that each time said button on said air pump is actuated, the pump supplies air to said second chamber and said displaceable wall is displaced progressively along the container such that analgesic liquid is driven out of said outlet of said first chamber along said catheter.

* * * * *